United States Patent [19]

Uchida et al.

[11] 4,314,011
[45] Feb. 2, 1982

[54] COLOR PHOTOGRAPHIC MATERIAL

[75] Inventors: Takashi Uchida; Takashi Sasaki; Shoji Kikuchi, all of Hino; Katsuo Mogaki, Odawara; Masahiko Taguchi, Odawara; Syun Takada, Odawara, all of Japan

[73] Assignee: Konishiroku Photo Industry Co., Ltd., Tokyo, Japan

[21] Appl. No.: 161,608

[22] Filed: Jun. 20, 1980

Related U.S. Application Data

[62] Division of Ser. No. 939,968, Sep. 6, 1978.

[30] Foreign Application Priority Data

Sep. 12, 1977 [JP] Japan .................. 52-110363

[51] Int. Cl.³ .............................................. G03C 5/24
[52] U.S. Cl. .................................................... 430/17
[58] Field of Search ........................ 430/17, 372, 551

[56] References Cited

U.S. PATENT DOCUMENTS

| 2,304,940 | 12/1942 | Mannes et al. | 430/549 |
| 2,735,765 | 2/1956 | Loria et al. | 430/551 |
| 3,183,219 | 5/1965 | Schuler | 430/512 |
| 3,698,909 | 10/1972 | Lestina et al. | 430/372 |
| 3,785,827 | 1/1974 | Piller et al. | 430/512 |
| 3,825,426 | 7/1974 | Pollett et al. | 430/568 |
| 3,973,979 | 8/1976 | Meier et al. | 430/554 |
| 4,010,036 | 3/1977 | Suga et al. | 430/265 |

FOREIGN PATENT DOCUMENTS

| 2733 | 2/1976 | Japan . |
| 14751 | 9/1977 | Japan . |
| 1353064 | 5/1974 | United Kingdom . |
| 1374779 | 11/1974 | United Kingdom . |
| 1374780 | 11/1974 | United Kingdom . |
| 1409089 | 10/1975 | United Kingdom . |

Primary Examiner—J. Travis Brown
Attorney, Agent, or Firm—Frishauf, Holtz, Goodman & Woodward

[57] ABSTRACT

A color photographic material comprising a support and at least one layer thereon containing at least one compound of formula [I]: Formula [I]

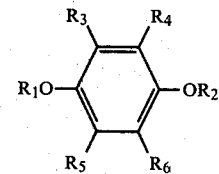

wherein $R_1$, $R_2$, $R_3$, $R_4$, $R_5$ and $R_6$ each are defined in the specification and claims of this application.

The compound of formula [I] is incorporated in a color photographic material to prevent the discoloration and fading-in-color of the color photographic material.

5 Claims, No Drawings

COLOR PHOTOGRAPHIC MATERIAL

This is a division of application Ser. No. 939,968 filed Sept. 6, 1978.

This invention relates to a color photographic material. More particularly, it relates to a color photographic material in which are prevented discoloration and color-fading caused by light in a dye image part and an unexposed part obtained by processing a light-sensitive silver halide color photographic material.

It is well-known that color images are formed by the reaction of couplers with an oxidation product of an aromatic primary amine, which product was produced by developing exposed silver halide grains in a light sensitive silver halide color photographic material by using an aromatic primary amine.

In this process, there have usually been used a compound having an open-chain active methylene group as a yellow coupler for forming a yellow dye; a compound having a pyrazolone, pyrazolinobenzimidazole, indazolone or pyrazolotriazole nucleus in which is comprised a closed-chain methylene group as a magenta coupler for forming a a magenta dye. All of these compounds forms azomethine dyes by the reaction with an oxidation product of an aromatic primary amine. As a cyan coupler for forming a cyan dye, there have generally been used phenols or α-naphthols having a phenolic hydroxyl group which form indoaniline type dyes by the reaction with an oxidation product of an aromatic primary amine.

It is desired that the dye images obtained from such couplers are stable even at high temperature or humidity, and do not discolor and fade in color when exposed to light for a long period of time. But their fastness (referred to as light resistance) mainly against ultraviolet rays or visible ray have not been satisfactory yet and it is known that irradiation by actinic rays dye images causes comparatively easy discoloration. To avoid such defects, there have been known various methods for improving the light resistance by using couplers with a smaller amount of discoloration; by using a ultraviolet absorber to protect dye images from ultraviolet ray; by adding anti-fading agent to prevent the fading by light; or by introducing a group which gives light-resistance into a coupler molecule. But for obtaining satisfactory light resistance of the dye images by using ultraviolet absorbers, a relatively large amount of them is needed and often results in staining of dye images due to coloration from the ultraviolet absorbers themselves. Using ultraviolet absorbers also has no effect on anti-fading of dye images due to visible light and has a limit for improving the light resistance with ultraviolet absorbers. There have further been known various anti-fading agents for dye images which have therein a phenolic hydroxyl group or a group producing a phenolic hydroxyl group when subject to hydrolysis. For example, in Japanese Patent Publications Nos. 31256/1973, 31625/1973 and 30462/1976, and Japanese Laid Open to Public Patent Publication Nos. 134326/1974 and 134327/1974 have been proposed phenols and bisphenols; pyrogallol, garlic acid and its esters in U.S. Pat. No. 3,069,262; α-tocopherols and their acyl derivatives in U.S. Pat. Nos. 2,360,290 and 4,015,990; hydroquinone derivatives in Japanese Patent Publication No. 27534/1977, Japanese Laid Open to Public Patent Publication No. 4751/1977 and U.S. Pat. No. 2,735,765; 6-hydroxychromans in U.S. Pat. Nos. 3,432,300 and 3,574,627; 5-hydroxy-cumarans in U.S. Pat. No. 3,573,050; and 6,6'-dihydroxy-2,2'-bisspirochromans in Japanese Patent Publication No. 20977/1974.

Although these compounds have some effect on the light resistance of dye images, their effects is not sufficient. The anti-fading effect is reduced or extinguished rapidly at a certain time during the preservation of a color photographic material for a long period of time. Furthermore, in some cases, the so-called after-yellowing (hereinafter called "Y-stain") owing to the actinic ray is brought about in the portions of the processed color photographic material where unreacted couplers remain, i.e. unexposed areas of the material. Some of these compounds have little solubility in the solvent used when they are added to a color photographic material. Due to the diffusibility, some of these compounds diffuse into a processing solution having high pH value. Although some of these compounds show an anti-fading effect on the color dye images obtained from yellow and cyan couplers, they do not show any anti-fading effect on the color dye images obtained from magenta couplers. Some of these compounds have no effect on the color dye image obtained from yellow and cyan couplers or sometimes accelerate the fading, although they have relatively excellent anti-fading effect on the color dye images obtained from megenta couplers. In the specifications of Japanese Laid Open to Public Patent Publication (hereinafter referred to as JLOP) Nos. 37636/1972 and 20723/1975, U.S. Pat. Nos. 3,519,429 and 3,880,661, there have been proposed couplers in which a group giving light resistance is introduced into the molecule. These couplers, however, are disadvantageous in that, although they are effective against ultraviolet ray, they show insufficient anti-fading effect against visible ray; and since they are unstable in a highly alkaline solution such as a color developer, side-reactions occur. Further, they are insufficient in properties important to color photography, i.e., the properties of the couplers themselves; color developability, solubility in an organic solvent, dispersion-stability in a silver halide emulsion, color density, etc. The light-absorption bands sometimes shift from the desired range of wave length. Inconvenience is caused because of the undesirable ratio of the coupler part and the anti-fading part. Further, the syntheses of these couplers require very complicated procedure, it is difficult to apply these couplers practically. Thus, these couplers are not satisfactory at this time.

The object of this invention is to provide a color photographic material which comprises an anti-fading agent which possesses an excellent anti-fading effect, an excellent solubility in a high-boiling solvent, etc., an excellent dispersion-stability and an excellent non-diffusibility; does not affect badly other photographic additives; and does not cause the inhibition of coloration of couplers.

As a result of extensive research, the present inventors have found that the above mentioned object can be accomplished by using a color photographic material comprising a layer containing at least one compound represented by following formula [I]:

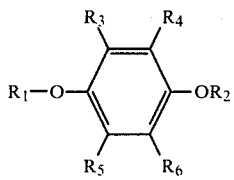

[I]

Wherein $R_1$ and $R_2$ each represent an alkyl group, an alkenyl group, a cycloalkyl group, an aryl group or a heterocyclic ring; $R_3$, $R_4$, $R_5$ and $R_6$ each represent hydrogen or halogen, or an alkyl group, an alkenyl group, a cycloalkyl group, an aryl group, an alkoxy group, an alkylthio group, an aryloxy group, an arylthio group, an acyl group, an acylamino group, an alkylamino group, an alkoxycarbonyl group or a sulfonamido group; and when both of $R_1$ and $R_2$ are alkyl groups, the total carbon number of the alkyl groups is not less than 3.

In formula [I], the halogen may be fluorine, chlorine, bromine or iodine; the alkyl group may be a straight-chain or branched one having preferably 1 to 32 carbon atoms, e.g., methyl, ethyl, n-butyl, t-butyl, 2-ethylhexyl, 3,5,5-trimethylhexyl, 2,2-dimethylpentyl, n-octyl, t-octyl, n-dodecyl, sec-dodecyl, n-hexadecyl, n-octadecyl, eicosyl, etc., the alkenyl group may be a straight-chain or branched one having preferably 2 to 32 carbon atoms, e.g., allyl, butenyl, octenyl, oleyl, etc.; the cycloalkyl group may preferably contain 5 to 7 ring members, e.g., cyclopentyl, cyclohexyl, cycloheptyl, etc.; the aryl group may be exemplified by phenyl, naphthyl, etc.; the heterocyclic ring may preferably be a 5 or 6-membered heterocyclic ring having one or more nitrogen, oxygen and/or sulfur atoms, e.g., furyl, pyranyl, tetrahydropyranyl, imidazolyl, pyrrollyl, pyrimidyl, pyradinyl, triazinyl, thienyl, quinolyl, oxazolyl, thiazolyl pyridyl, etc.

As the alkoxy group (preferably 1 to 32 carbon atoms) may be mentioned for example methoxy, ethoxy, n-propoxy, t-butoxy, n-hexoxy, n-dodecoxy, n-octadecoxy, n-docosoxy, etc.; as the alkylthio group, e.g., methylthio, n-butylthio, n-octylthio, n-dodecylthio, n-docosylthio, etc.; as the aryloxy group, e.g., phenoxy, naphthoxy, etc.; as the arylthio group, e.g., phenylthio etc.; as the acyl group, e.g., acetyl, butanoyl, octanoyl, dodecanoyl, benzoyl, cinnamoyl or naphthoyl, etc.; as the acylamino group, e.g., acetylamino, octanoylamino, benzoylamino, etc.; as the alkylamino group, mono- or dialkylamino such as methylamino, ethylamino, diethylamino, isopropylamino, di-n-octylamino, di-n-decylamino, etc.; as the alkoxycarbonyl group, e.g., methoxylcarbonyl, ethoxycarbonyl, n-nonyloxycarbonyl, n-hexadecyloxycarbonyl, n-docosyloxycarbonyl, etc.; as the sulfonamido group, e.g., methylsulfonamido, octylsulfonamido, phenylsulfonamido, etc. In formula (I), $R_1$ and $R_2$ each may preferably be a straight-chain or branched alkyl or alkenyl group having 1 to 32 carbon atoms. $R_3$, $R_4$, $R_5$ and $R_6$ each may preferably be hydrogen, straight-chain or branched alkyl or alkenyl having 1 to 32 carbon atoms, or an alkoxy group having 1 to 8 carbon atoms.

Particularly preferable is the case where at least one of $R_1$ and $R_2$ is an alkyl group having 8 to 32 carbon atoms; and at least two of $R_3$, $R_4$, $R_5$ and $R_6$ are an alkyl group (preferably 1 to 8 carbon atoms), an alkenyl group (preferably 2 to 8 carbon atoms) or an alkoxy group (preferably 1 to 8 carbon atoms) and the other two groups (particularly $R_4$ and $R_5$) are hydrogen atoms.

The groups and ring appeared in the general formula (I) include the substituents which do not substantially react with the oxidized form of a developer to form a coloring dye as explained before.

Said substituents mean groups containing no active methylene and active methine groups therein.

Although the substituents may be any substituents, preferred ones are one or more appropriately selected from the group consisting of halogen, hydroxyl, carboxy, sulfo, cyano, alkyl (having preferably 1 to 32 carbon atoms) group, alkenyl (having preferably 2 to 32 carbon atoms) group, alkoxy group, alkylthio group, alkenyloxy group, alkenylthio group, aryl group, aryloxy group, arylthio group, arylamino group, alkylamino group, alkenylamino group, acyl group, acyloxy group, acylamino group, carbamoyl group, sulfonamido group, sulfamoyl group, alkoxycarbonyl group, aryloxycarbonyl group and heterocyclic ring (preferably of 5 to 6 ring members having nitrogen, oxygen and/or sulfur atoms) among which hydroxyl, cyano, carboxy, halogen, an aryl group, an alkoxy group having 1 to 32 carbon atoms, an aryloxy group and an alkoxycarbonyl group having 1 to 32 carbon atoms are more preferred.

The representative and concrete examples of the compound of this invention will be shown below, which, however, should not be construed to restrict the compound used in this invention.

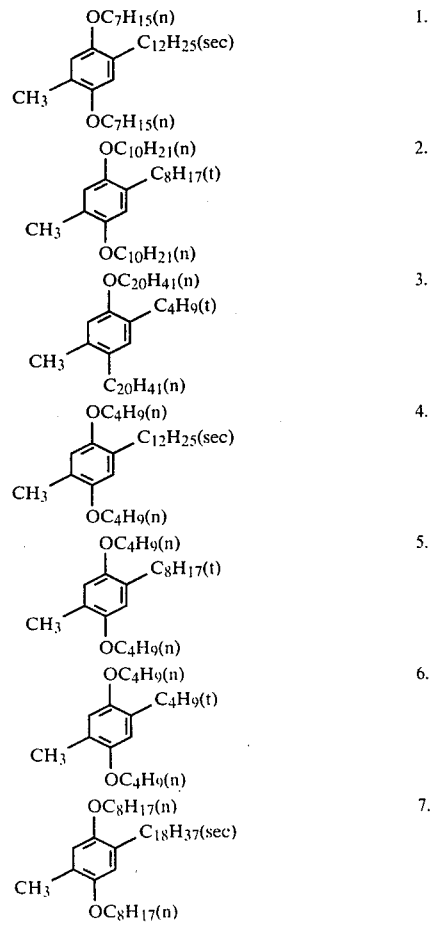

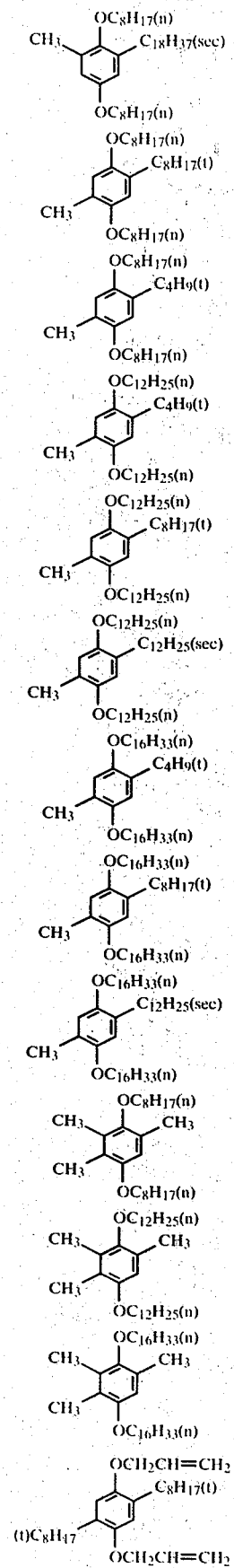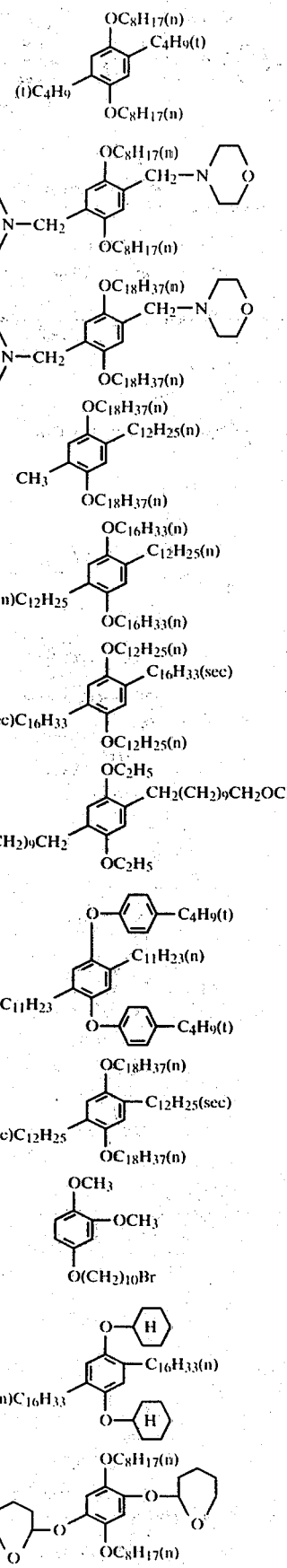

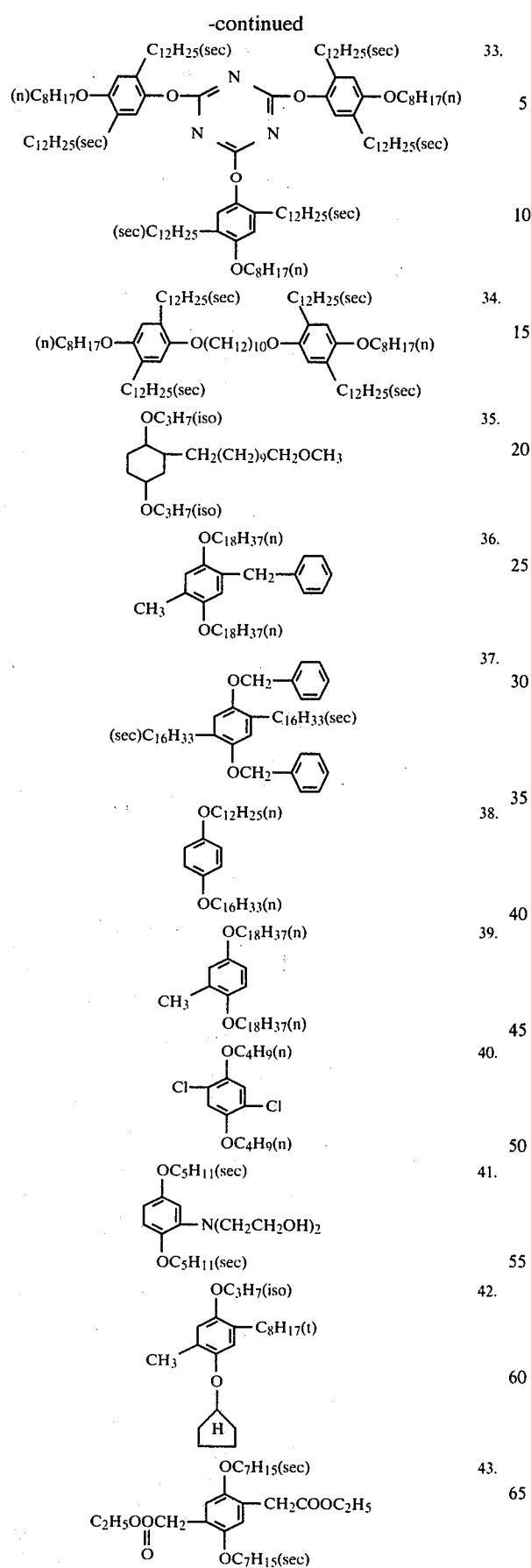
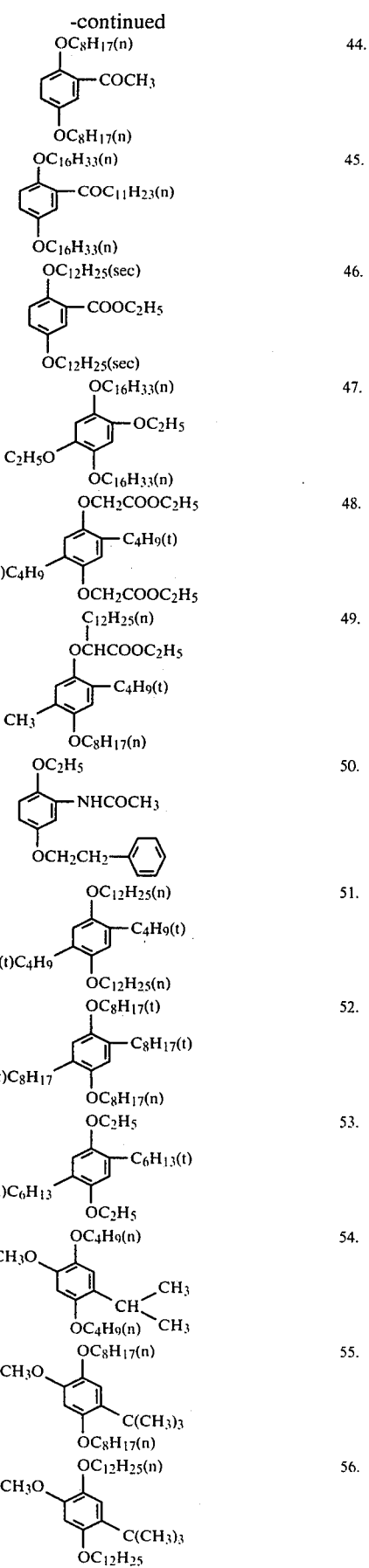

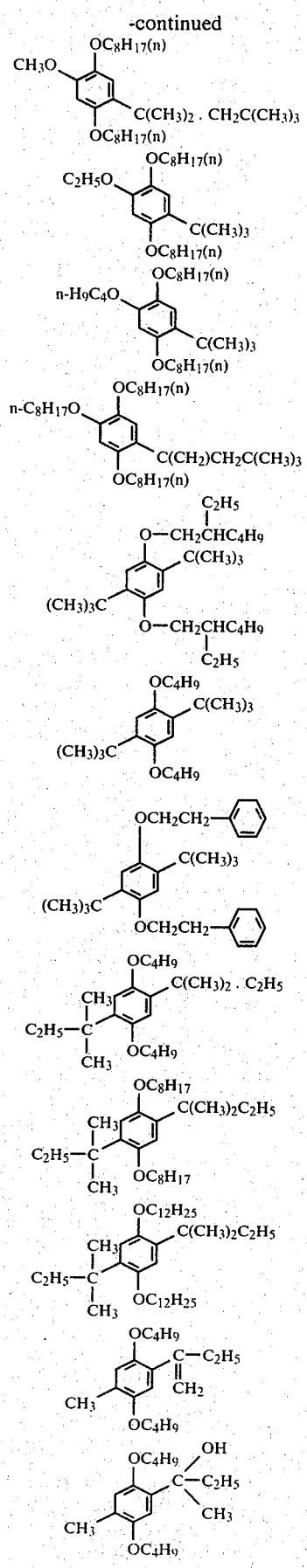

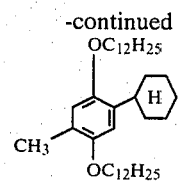

The compounds of this invention can easily be synthesized by the methods described in Journal of the Chemical Society, pages 2904–2914 (1965) and Journal of Organic Chemistry, vol. 23, pages 75–76.

Examples of syntheses will be illustrated below. These examples show, only for reference, representative and concrete examples of compounds synthesized by general methods including the synthetic methods described in the above-mentioned literatures.

Synthesis-1 (Synthesis of exemplified compound No. 4)

In 500 ml of ethanol was dissolved 27.1 g of potassium hydroxide. In the resulting solution were further dissolved 50 g of 2-methyl-5-secdodecylhydroquinone and 56 g of butyl bromide, and the solution was heated under reflux. After two hours, the inorganic substance formed was removed by filtration and the solvent was distilled off from the filtrate. Distillation of the residue gave a product boiling at 158°–162° C./0.2 mmHg.

The product was identified to be the desired one by its boiling point (BP), infrared absorption spectrum (IR), nuclear magnetic resonance spectrum (NMR), mass spectrum (MS) and the result of its elementary analysis. The desired product was confirmed to be a mixture of several isomers.

Elementary Analysis (for $C_{27}H_{48}O_2$) (unit:%): Calcd.: C: 80.14; H: 11.96. Found: C: 80.40; H: 12.23.

Synthesis-2 (Synthesis of exemplified compound No. 7)

In 15 l of ethanol was dissolved 843 g of potassium hydroxide, and 2,000 g of 2-methyl-5-secoctadecylhydroquinone and 2,460 g of octyl bromide were added thereto. The resulting mixture was heated for 3.5 hours under reflux with stirring. After reaction, inorganic substances were filtered off. After evaporating the solvent from the filtrate, the residue was distilled under reduced pressure to give a product boiling at 205°–210° C./0.2 mmHg. The product was identified to be the desired one by its BP, IR and the result of its elementary analysis.

Elementary Analysis (for $C_{41}H_{76}O_2$) (unit: %): Calcd.: C: 81.93; H: 12.75. Found: C: 82.08; H: 12.91.

Synthesis-3 (Synthesis of exemplified compound No. 8)

In 500 ml of ethanol was dissolved 168.6 g of potassium hydroxide, and 400 g of 2-methyl-6-secoctadecylhydroquinone and 492 g of octyl bromide were dissolved therein. The resulting solution was refluxed under heating with stirring for 4 hours. After reaction, inorganic substances formed were filtered off. Then the filtrate was condensed by evaporating the solvent and the residue was distilled under reduced pressure to give a very viscous substance boiling at 199°–206° C./0.05 mmHg. The product was identified to be the desired one by means of BP, NMR, IR and the result of its elementary analysis.

Elementary Analysis (for $C_{41}H_{76}O_2$) (unit: %): Calcd.: C: 81.93; H: 12.75. Found: C: 82.11; H: 12.92.

Synthesis-4 (Synthesis of exemplified compound No. 11)

In 2,000 ml of n-hexane was dissolved 2,300 g of 2,5-di-dodecyloxytoluene, and 100 ml of concentrated sulfuric acid was added thereto. The resulting mixture was heated at 50° C. with stirring and then isobutene was absorbed therein. After completion of the reaction, the n-hexane was removed by distillation under reduced pressure and the residue was washed with methanol to give an oil. The oil was crystallized by cooling and then recrystallized from acetone to give white needles melting at 40°–41.5° C. The product was identified to be the desired one by means of its melting point (MP), NMR, IR and the result of its elementary analysis.

Elementary Analysis (for $C_{35}H_{64}O_2$) (unit: %): Calcd.: C: 81.33; H: 12.48. Found: C: 81.51; H: 12.64.

Synthesis-5 (Synthesis of exemplified compound No. 16)

In 500 ml of ethanol was dissolved 27.1 g of potassium hydroxide, and 50 g of 2-methyl-5-secdodecylhydroquinone and 125 g of hexadecyl bromide were added thereto. The resulting mixture was heated under reflux with stirring. After 2 hours the solvent was removed by distillation and then the resulting residue was dissolved in ligroin. After removing the salt formed by filtration, the ligroin was removed by distillation from the filtrate. The black residue thus obtained was purified by column chromatography (silica gel: 200 mesh, developing solvent: n-hexane) to give a light yellow liquid. The product was identified to be the desired one by means of IR, NMR and the result of its elementary analysis. Further, the desired product was found to be a mixture of several isomers.

Elementary Analysis (for $C_{51}H_{96}O_2$) (unit: %): Calcd.: C: 82.63; H: 13.05. Found: C: 82.89; H: 13.27.

Synthesis-6 (Synthesis of exemplified compound No. 17)

In 10 of ethanol was dissolved 480 g of an aqueous solution of potassium hydroxide. To the resulting solution were added 500 g of trimethylhydroquinone and 1,410 g of octyl bromide, and the mixture was refluxed under heating for 3.5 hours. After reaction, the ethanol was removed from the reaction mixture by distillation, water was added to the residue and the mixture was extracted with n-hexane. After the n-hexane layer was washed with a around-10% aqueous sodium hydroxide and then with water, the layer was condensed by evaporation under reduced pressure. The residue thus obtained was evaporated under reduced pressure to give a light yellow highly viscous product melting at 213°–218° C./3 mmHg. The product was identified to be the desired one by means of MP, NMR, IR, MS and the result of its elementary analysis.

Elementary Analysis (for $C_{25}H_{44}O_2$) (unit:%): Calcd.: C: 79.73; H: 11.78. Found: C: 79.93; H: 11.87.

Synthesis-7 (Synthesis of exemplified compound No. 23)

In 8 l of ethanol was dissolved 320 g of potassium hydroxide. To the resulting solution were added 640 g of 2,5-di-morpholinomethyl-hydroquinone and 960 g of octadecyl bromide, and the resulting mixture was heated under reflux for 4 hours. After reaction, the inorganic substances formed were removed by filtration and the filtrate was cooled to give white needles melting at 66°–68° C. The product was identified to be the desired one by means of MP, NMR, IR and the result of its elementary analysis.

Elementary Analysis (for $C_{52}H_{96}N_2O_4$) (unit: %): Calcd.: C: 76.79; H: 11.90; N: 3.44. Found: C: 76.94; H: 11.99; N: 3.47.

Synthesis-8 (Synthesis of exemplified compound No. 53)

In 1,500 ml of ethyl acetate was dissolved 664 g of hydroquinone diethyl ether, and 600 ml of concentrated sulfuric acid was gradually added thereto. Further, 740 g of 2-methyl-1-pentene was added thereto and the mixture was heated under reflux for 7 hours. Then, the solvent was removed from the reaction mixture by distillation and 2,500 ml of methanol was added to the resulting liquid to precipitate white crystals. The thus obtained crystals were recrystallized to obtain the desired white needles melting at 76°–77° C. The product was confirmed to be the desired one by means of MP, NMR, IR, MS and the result of its elementary analysis.

Elementary Analysis (for $C_{22}H_{38}O_2$) (unit: %): Calcd.: C: 78.98; H: 11.45. Found: C: 89.21; H: 11.48.

Although a little effect was observed in a compound where $R_1$ and $R_2$ of the above-mentioned formula (I) each represent an alkyl group and the total number of carbon atoms of $R_1$ and $R_2$ is not more than 2, the extent of the effect is too low to attain the object of this invention.

The compound of this invention may be incorporated in any layer constituting a color photographic material. It may preferably be incorporated in yellow-, magenta- and cyan- dye-image-forming layers. It may also be incorporated in other layers, for example, a layer adjacent to these dye-image-forming layers.

The color photographic material according to this invention may comprise only one layer, preferably multiple layers including separate layers which individually form yellow, magenta and cyan dye images. Not only one layer may be included in each yellow, magenta and cyan dye-image-forming layers, but also not less than 2 layers may be included therein.

In order to incorporate the compound of this invention in the layer or layers constituting a color photographic material, the following methods may generally be applied.

According to methods described in U.S. Pat. Nos. 2,322,027, 2,801,170, 2,801,171, 2,272,191 and 2,304,940, the compounds of formula (I) according to this invention, which are soluble in oil, are preferably dissolved in a high-boiling point solvent, in combination of a low-boiling point solvent, if necessary, together with a low-boiling point solvent, and then dispersed and incorporated into a silver halide emulsion. If necessary, couplers, hydroquinone derivatives, ultraviolet absorber and known anti-fading agents for dye images may be added together. In this case, two or more of the compounds of formula (I) according to this invention may be used in combination. The incorporation method of the compounds of this invention will be described in detail as follows: one or more of the compounds together with couplers, hydroquinone derivatives and an ultraviolet absorber and/or known anti-fading agent for dye images, if necessary, are dissolved in a high-boiling point solvent such as organic acid amides, carbamates, esters, ketones, hydrocarbons and urea derivatives, especially di-n-butyl phthalate, tricresyl phosphate, di-isooctyl azelate, di-n-butyl sebacate, tri-n-hexyl phosphate, decalin, N,N-diethyl-caprylamidobutyl, N,N-diethyl laurylamide, n-pentadecylphenyl ether or a fluorinated paraffin; or, if necessary, in a low-boiling point solvent such as ethyl acetate, butyl acetate, butyl propionate, cyclohexanol, cyclohexane or tetrahydrofuran (these high-boiling and low-boiling point solvents may be used singly or in combination); and the solution is then mixed with an aqueous solution containing a hydrophilic binder such as gelatin which comprises an anionic surface active agent such as alkylbenzenesulfonic acid, and alkylnaphthalene sulfonic acid and/or a nonionic surface active agent such as solbitan sesquioleate ester and solbitan monolaurate ester and the resulting mixture is emulsified by means of a high-speed mixer, a colloid mill or an ultra sonic dispersion apparatus and then is incorporated into a hydrophilic colloidal solution.

The thus obtained hydrophilic colloidal solution is coated (after incorporation of silver halide as mentioned hereinafter, in cases where said hydrophilic colloidal solution is a silver halide emulsion) by various methods to prepare a silver halide lightsensitive color photographic material. Then, the silver halide light-sensitive color photographic material is subjected to photographic processing as mentioned hereinafter to obtain a color photographic material.

Further, the compounds of this invention may also be dispersed easily in accordance with the dispersion methods described in the specifications of U.S. Pat. Nos. 2,269,158, 2,852,382, 2,772,168, 3,619,195 and 2,801,170, and JLOP Nos. 59942/1976, 59943/1976, 74538/1974, 17637/1975, 25132/1976, 110327/1976 and so on, in which methods are used latex solutions.

Among the compounds of this invention, those which is soluble in an alkaline aqueous solution (or in water) may also be added to the hydrophilic colloidal solution after dissolved in an alkaline aqueous solution (or in water).

The compounds of this invention also show sufficient effect when incorporated into a color photographic material which was obtained after photographic processing of a silver halide light-sensitive color photographic material.

It is preferable that the compound of this invention is added to and incorporated in a silver halide emulsion by dispersing it together with lipophilic photographic additives, such as couplers, etc., in accordance with the method as mentioned above. It is particularly preferable to incorporate it in a green sensitive emulsion layer containing a coupler which forms a magenta dye image. The compound of this invention is particularly effective when it is used with a 5-pyrazolone coupler among the couplers which form magenta dye images.

The amount of the present compound to be added is not limited in particular since the compound is substantially colorless and does not have bad influence such as coloring pollution and the like. From a mainly economical point of view, it is preferable to use it in an amount of 5 to 500 mol.%, more preferably 10 to 50 mol.% against a coupler used in cases where it is used for a silver halide light-sensitive color photographic material containing a coupler. In cases where it is used for a silver halide light-sensitive color photographic material containing no coupler, it is preferably used in an amount of 0.1 to 1 mole, particularly 0.15 to 0.6 mole per one mole of silver halide.

It is advantageous to prevent the discoloration by an actinic ray of short wave length by using an ultraviolet absorber such as thiazolidones, benzotriazoles, acrylonitriles and benzophenones.

It is particularly advantageous to use Tinuvin PS, Tinuvin 320, Tinuvin 326, Tinuvin 327 and Tinuvin 328 singly or in combination.

Any coupler which forms dye images can be used for the silver halide light-sensitive color photographic material of this invention.

As the couplers which forms yellow dye images may be mentioned a benzoylacetanilide coupler, pivaloylacetanilide coupler or a two-equivalent dye-forming coupler in which the carbon atom at the coupling site is connected with a substituent (so-called split-off group) which can be split off during the coupling reaction. As the couplers which form magenta dye images may be mentioned a 5-pyrazolone coupler, a pyrazolotriazole coupler, a pyrazolinobenzimidazole coupler, an indazolone coupler or a two-equivalent magenta-dye-forming coupler having a split-off group. As the couplers which form cyan dye images may be mentioned a phenol coupler, a naphthol coupler, a pyrazoloquinazolone coupler or a two-equivalent cyan-dye-image-forming coupler.

Representative examples of dye-image-forming couplers used in this invention will be shown below, which, however, should not be construed to limit the present invention.

(Y-1) α-(4-carboxyphenoxy)-α-pivalyl-2-chloro-5-[γ-(2,4-di-t-amylphenoxy)butylamido]acetonilide (Y-2) α-benzoyl-2-chloro-5-[γ-(2,4-di-t-amylphenoxy)butylamido]acetonilide (Y-3) α-benzoyl-2-chloro-5-[α-(dodecyloxycarbonyl)ethoxycarbonyl]acetanilide (Y-4) α-(4-carboxyphenoxy)-α-pivalyl-2-chloro-5-[α-(3-pentadecylphenoxy)butyramido]acetanilide (Y-5) α-(1-benzyl-2,4-dioxo-3-imidazolydinyl)-α-pivalyl-2-chloro-5-[γ-(2,4-di-t-amylphenoxy)butyramido]acetanilide (Y-6) α-[4-(1-benzyl-2-phenyl-3,5-dioxo-1,2,4-triazolidinyl)]-α-pivalyl-2-chloro-5-[γ-(2,4-di-t-amylphenoxy)butyramido]acetanilide (Y-7) α-acetoxy-α-{3-[α-(2,4-di-t-amylphenoxy)butyramido]benzoyl}-2-methoxyacetanilide (Y-8) α-{3-[α-(2,4-di-t-amylphenoxy)butyramido]benzoyl}-2-methoxyacetanilide (Y-9) α-[4-(4-benzyloxyphenylsulfonyl)phenoxy]-α-pivalyl-2-chloro-5-[γ-(2,4-di-t-amylphenoxy)butyramido]acetanilide (Y-10) α-pivalyl-α-(4,5-dichloro-3(2H)-pyridazo-2-yl)-2-chloro-5-[(hexadecyloxycarbonyl)methoxycarbonyl]acetanilide (Y-11) α-pivalyl-α-[4-(p-chlorophenyl)-5-oxo-Δ$^2$-tetrazolin-1-yl]-2-chloro-5-[α-(dodecyloxycarbonyl)ethoxycarbonyl]acetanilide (Y-12) α-(2,4-dioxo-5,5-dimethyloxazolidin-3-yl)-α-pivalyl-2-chloro-5-[α-(2,4-di-t-amylphenoxy)butyramido]acetanilide (Y-13) α-pivalyl-α-[4-(1-methyl-2-phenyl-3,5-

| | -continued |
|---|---|
| (Y-14) | dioxo-1,2,4-triazolidinyl)]-2-chloro-5-[γ-(2,4-di-t-amylphenoxy)butyramido]acetanilide |
| (M-1) | α-pivalyl-α-[4-(p-ethylphenyl)-5-oxo-Δ²-tetrazolyl-1-yl]-2-chloro-5-[γ-(2,4-di-t-amylphenoxy)butyramido]acetanilide |
| (M-2) | 1-(2,4,6-trichlorophenyl)-3-[3-(2,4-di-t-amylphenoxyacetamido)benzamido]-5-pyrazolone |
| (M-3) | 1-(2,4,6-trichlorophenyl)-3-(3-dodecylsuccinimidobenzamido)-5-pyrazolone |
| (M-4) | 4,4'-methylenebis{1-(2,4,6-trichlorophenyl)-3-[3-(2,4-di-t-amylphenoxyacetamido)benzamido]-5-pyrazolone} |
| (M-5) | 1-(2,4,6-trichlorophenyl)-3-(2-chloro-5-octadecylsuccinimidoanilino)-5-pyrazolone |
| (M-6) | 1-(2-chloro-4,6-dimethylphenyl)-3-{3-[α-(3-pentadecylphenoxy)butyramido]benzamido}-5-pyrazolone |
| (M-7) | 1-(2,4,6-trichlorophenyl)-3-(2-chloro-5-octadecylcarbamoylamilino)-5-pyrazolone |
| (M-8) | 3-ethoxy-1-{4-[α-(3-pentadecylphenoxy)butyramido]phenyl}-5-pyrazolone |
| (M-9) | 1-(2,4,6-trichlorophenyl)-3-(2-chloro-5-tetradecanamidoanilino)-5-pyrazolone |
| (M-10) | 1-(2,4,6-trichlorophenyl)-3-{2-chloro-5-[α-(3-t-butyl-4-hydroxyphenoxy)tetradecanamido]anilino}-5-pyrazolone |
| (M-11) | 1-(2,4,6-trichlorophenyl)-3-[3-(2,4-di-t-amylphenoxyacetamido)benzamido]-4-acetoxy-5-pyrazolone |
| (M-12) | 1-(2,4,6-trichlorophenyl)-3-[3-(2,4-di-t-amylphenoxyacetamido)benzamido]-4-ethoxycarbonyloxy-5-pyrazolone |
| (M-13) | 1-(2,4,6-trichlorophenyl)-3-[3-(2,4-di-t-amylphenoxyacetamido)benzamido]-4-(4-chlorocinnamoyloxy)-5-pyrazolone |
| (M-14) | 4,4'-benzylidenebis[(1-(2,4,6-trichlorophenyl)-3-{2-chloro-5-[γ-(2,4-di-t-amylphenoxy)butyramido]anilino}-5-pyrazolone)] |
| (M-15) | 4,4'-benzylidenebis[(1-(2,3,4,5,6-pentachlorophenyl)-3-{2-chloro-5-[γ-(2,4-di-t-amylphenoxy)butyramido]anilino}-5-pyrazolone)] |
| (M-16) | 4,4'-(2-chloro)benzylidenebis[1-(2,4,6-trichlorophenyl)-3-(2-chloro-5-dodecylsuccinimidoanilino-5-pyrazolone] |
| (M-17) | 4,4'-methylenebis[(1-(2,4,6-trichlorophenyl)-3-{3-[α-(2,4,-di-t-amylphenoxy)butyramido]benzamido}-5-pyrazolone)] |
| (M-18) | 1-(2,6-dichloro-4-methoxyphenyl)-3-(2-methyl-5-acetamidoanilino)-5-pyrazolone |
| (M-19) | 1-(2-chloro-4,6-dimethylphenyl)-3-(2-methyl-5-chloroanilino)-5-pyrazolone |
| (M-20) | 1-(2,4,6-trichlorophenyl)-3-(4-nitroanilino)-5-pyrazolone |
| (M-21) | 1-(2,4,6-trichlorophenyl)-3-(2-chloro-5-octadecenylsuccinimido-anilino)-5-pyrazolone |

| | -continued |
|---|---|
| (C-1) | 1-(2,4,6-trichlorophenyl)-3-(2-chloro-tridecanamidoanilino)-5-pyrazolone |
| (C-2) | 1-hydroxy-N-[δ-(2,4-di-t-amylphenoxy)butyl]-2-naphthamide |
| (C-3) | 2,4-dichloro-3-methyl-6-(2,4-di-t-amylphenoxyacetamido)phenol |
| (C-4) | 2,4-dichloro-3-methyl-6-[α-(2,4-di-t-amylphenoxy)butyramido]phenol |
| (C-5) | 1-hydroxy-4-(3-nitrophenylsulfonamido)-N-[δ-(2,4-di-t-amylphenoxy)butyl]-2-naphthamide |
| (C-6) | 1-hydroxy-4-[(β-methoxyethyl)carbamoyl]methoxy-N-[δ-(2,4-di-t-amylphenoxy)butyl]-2-naphthamide |
| (C-7) | 1-hydroxy-4-(isopropylcarbamoyl)methoxy-N-dodecyl-2-naphthamide |
| (C-8) | 2-perfluorobutyramido-5-[α-(2,4-di-t-amylphenoxy)hexanamido]phenol |
| (C-9) | 1-hydroxy-4-(4-nitrophenylcarbamoyl)oxy-N-[δ-(2,4-di-t-amylphenoxy)butyl]-2-naphthamide |
| (C-10) | 2-(α,α,β,β-tetrafluoropropionamido-5-[α-(2,4-di-t-amylphenoxy)butyramido]phenol |
| (C-11) | 1-hydroxy-N-dodecyl-2-naphthamide |
| (C-12) | 1-hydroxy-(4-nitro)phenoxy-N-[δ-(2,4-di-t-amylphenoxy)butyl]-2-naphthamide |
| (C-13) | 1-hydroxy-4-(1-phenyl-5-tetrazolyloxy)-N-[δ-(2,4-di-t-amylphenoxy)butyl]-2-naphthamide |
| (C-14) | 2-(α,α,β,β-tetrafluoropropionamido)-4-β-chloroethoxy-5-[α-(2,4-di-t-amylphenoxy)butyramido]phenol |
| | 2-chloro-3-methyl-4-ethylcarbamoylmethoxy-6-[α-(2,4-di-t-amylphenoxy)butyramido]phenol |

The couplers used in light-sensitive silver halide color photographic materials according to this invention are usually used within a range of 5 to 50 mol.% per silver halide, preferably 10 to 30 mol.%. When used in a developer, they are used in a concentration range of about 0.5 to 3.0 g/l, preferably about 1.0 to 2.0 g/l. In these cases, they are used singly or in combination of two or more of them and even in the case of the combination use, the amount to be added is sufficient enough in the amount described above.

Silver halide emulsion can further comprises hydroquinone derivatives which have been well known as antistain agents. Among these hydroquinone derivatives, those having substituted or unsubstituted alkyl group on their aromatic nuclei are effective and the most preferred compounds are 2,5-dioctylhydroquinone, 2,5-di-tert-amylhydroquinone, 2,5-di-tert-butylhydroquinone, etc.

Silver halide emulsions according to this invention are those in which silver halide particles are generally dispersed in a hydrophilic colloid. Silver halides to be used are such as silver chloride, silver bromide, silver iodide, silver chlorobromide, silver iodobromide, silver chloroiodobromide and their mixtures and the silver halide can be prepared by means of various methods such as an ammonia method, a neutralization method, a so-called conversion method, a mixing simultaneous method, and the like. A hydrophilic colloid used for dispersion of these silver halides are generally gelatin, and/or gelatin derivatives such as phthalated gelatin and malonated gelatin. A part or all parts of the gelatin or gelatin derivative amount can be replaced with alubumin, agar, gum arabic, arginic acid, casein, partially hydrolyzed cellulose derivative, partially hydrolyzed polyvinyl acetate, polyacrylamide, imidated polyacrylamide, polyvinyl pyrrolidone and/or copolymer of these vinyl compounds. These silver halide emulsions can optically be sensitized by using various sensitizing dyes for providing sensitivity in desired sensitive wave length. As preferred sensitizing dyes, there can be used cyanine dyes, merocyanine dyes or complex cyanine dyes in single or in combination. If necessary, the following photographic additives can be added to silver halide emulsions in single or in combination: chemical sensitizers such as thioethers, quatenary ammonium chlorides and polyalkyleneoxide compounds; stabilizers such as triazoles, imidazoles, azaindenes, benzothiazolium compounds, zinc compounds, cadmium compounds, mercaptans; hardeners such as chromium salts, zirconium salts, and mucochloric acid, and such hardeners as aldehydes, triazines, polyepoxy compounds, triethylene-phosphonamides and ethyleneimines; plasticizers of dihydroxyalkanes such as glycerin and 1,5-pentandiol; fluorescent brightening agents; antistatic agents; coating aids. To the silver halide emulsion thus obtained, the compound having formula (I) according to this invention is ordinally dispersed. The so-dispersed emulsion is coated on a base such as cellulose acetate films, cellulose nitrate films, synthetic resin films such as films of polycarbonate, polyethyleneterephthalate or polystyrene, baryta papers, polyethylene coated papers, glass plate, etc.

The light-sensitive silver halide color photographic material can be either a coupler-in-emulsion type light sensitive silver halide color photographic material which contains couplers in advance and a coupler-out-emulsion type light-sensitive silver halide color photographic material which does not contain the coupler in advance but is processed by a developer containing the coupler. It, however, can be preferably applied to the former type and developed with a color development after exposure. It also can be a light sensitive silver halide color photographic material in which both a coupler and a color developing agent are located in the same layer in such a way as not to contact each other before exposure but to be allowed contact them after exposure; or a light-sensitive silver halide color photographic material obtaining a coupler, in which a color developing agent is contained in a layer not containing said coupler, but made in contact with said coupler when it is immersed in an alkaline processing solution. In a diffusion-transfer type light-sensitive silver halide color photographic material, the compounds having formula (I) according to this invention can be added to sensitive elements and/or receiving elements used for this kind of photography, preferably to the latter elements. In a reversal process, the present photographic material is, after imagewise exposed, developed with a black and white developing solution, then either exposed to white light or treated with a bath containing a fogging agent such as boron compound and thereafter color-developed with an alkaline developing solution containing a color developing agent. In this case, the fogging agent can be contained in the alkaline developing solution containing the color development agent without trouble. After color development, the photographic material is bleached with a bleaching solution containing ferricyanide or a ferric salt of an aminopolycarboxylic acid as an oxidant and fixed with a fixing solution containing a silver salt solvent such as thiosulfate so as to remove silver image and remained silver halide to remain dye image only. Instead of using both the bleaching and fixing solutions, it can also be bleached and fixed with a combined bleaching and fixing bath which is usually abbreviated as a blix. In combination of the steps of color development, bleaching, fixing or combined bleaching and fixing, it can also additionally be processed with various treatments such as prehardening, neutralization, water washing, stopping or stabilization. The preferred developing process of the light-sensitive silver halide color photographic material of this invention are, for example, color development, water washing, if necessary, bleaching and fixing, water washing, stabilization, if necessary, and drying in this order. This processing can be carried out at a high temperature over 30° C. and in an extremely short time. Representative processing and representative composition for each processing solution are shown as follows:

| Processing (at 30° C.) | Processing time |
| --- | --- |
| Color development | 3 min. 30 sec. |
| Bleaching and fixing | 1 min. 30 sec. |
| Water washing | 2 min. |
| Stabilization | 1 min. |
| Drying | |
| Composition of color developing solution: | |
| Benzyl alcohol | 5.0 ml |
| Sodium hexametaphosphate | 2.5 g |
| Anhydrous sodium sulfite | 1.9 g |
| Sodium bromide | 1.4 g |
| Potassium bromide | 0.5 g |
| Borax ($Na_2B_4O_7 \cdot 10H_2O$) | 39.1 g |
| N-ethyl-N-$\beta$-methansulfon-amidoethyl-4-aminoaniline sulfate | 5.0 g |
| Water to make | 1 l |
| pH was adjusted to pH 10.30 by using sodium hydroxide. | |
| Composition of bleaching and fixing solution: | |
| Iron ammonium ethylene-diaminetetraacetate | 61.0 g |
| Diammonium ethylenediamine-tetraacetate | 5.0 g |
| Ammonium thiosulfate | 124.5 g |
| Sodium metabisulfite | 13.3 g |
| Anhydrous sodium sulfite | 2.7 g |
| Water to make | 1 l |
| pH was adjusted to 6.5 by using ammonia | |
| Composition of stabilizer: | |
| Glacial acetic acid | 20 ml |
| 800 ml of water was added, and the solution was adjusted to pH 3.5 to 4.0 by using sodium acetate and made 1 l by water addition. | |

Useful color developing agents for color development of light-sensitive silver halide color photographic materials of this invention are such as primary phenylene diamines, aminophenols, and their derivatives. The representatives are as follows: inorganic acid salts such as salts of hydrochloric acid and sulfuric acid and organic acid salts such as salts of p-toluene-sulfonic acid, the salts being of N,N-dimethyl-p-phenylenediamine, N,N-diethyl-p-phenylenediamine, N-carbamidomethyl-N-methyl-p-phenylenediamine, N-carbamidomethyl-N- tetrahydrofurfuryl-2-methyl-p-phenylenediamine, N-ethyl-N-carboxymethyl-2-methyl-p-phenylenediamine, N-carbamidomethyl-N-ethyl-N-ethyl-2-methyl-p-phenylenediamine, N-ethyl-N-tetrahydrofurfuryl-2-methyl-p-aminophenol, 3-acetylamino-4-aminodimethylaniline, N-ethyl-N-β-methanesulfonamidoethyl-4-aminoaniline, N-ethyl-N-β-methanesulfonamidoethyl-3-methyl-4-aminoaline, N,N-diethyl-3-methyl-p-phenylenediamine and N-methyl-N-β-sulfoethyl-p-phenylenediamine. These color developing agents are used singly or in the combination of two or more of them.

Light-sensitive silver halide color photographic materials using the compounds of formula (I) can effectively be processed with a color developing solution containing both a primary aromatic amino type color developing agent and an oxidant which oxidant is to expose metal silver image to redox reaction.

In the case of using these color developing solutions, the color developing agents are oxidized with an oxidant and form dye images by coupling with photographic color couplers. Such color developing agents are disclosed in, for example, JLOP No. 9,729/1973 and preferred oxidants for this object are cobalt complexes having 6 coordination numbers. Color processing comprising the use of such color developing solutions are especially effective for a silver halide light-sensitive color photographic material in which a smaller amount of silver than that of ordinary light-sensitive silver halide color photographic materials is employed for the purpose of saving silver.

Especially useful cobalt complexes contain a ligand selected from the group consisting of ethylenediamine, diethylenetriamine, triethylenetetraamine, amine, nitrate, nitrite, azide, chloride, thiocyanate, isothiocyanate, water and carbonate and is further required to contain (1) at least two ligands of ethylenediamine, (2) at least five ligands of amine, or (3) at least one ligand of triethylenetetraamine. Especially preferred cobalt complexes are such as follows:

[Co(En)$_2$(N$_3$)$_2$]X; [Co(En)$_2$Cl(NCS)]X; [Co(En)$_2$(NH$_3$)N$_3$]X; [Co(En)$_2$Cl$_2$]X; [Co(En)$_2$(SCN)$_2$]X; [Co(En)$_2$(NCS)$_2$]X; and [Co(NH$_3$)$_6$]X.

In the above formulae, "En" represents ethylenediamine and X represents at least one cation selected from the group consisting of chloride, bromide, nitrate, nitrite, perchlorate, acetate, carbonate, sulfite, sulfate, hydrochloride, thiocyanate, isothiocyanate and hydroxide. Most preferred complexes are cobalt hexamine salts of such as chloride, bromide, sulfite, sulfate, perchlorate, nitrite and acetate. The amount of cobalt complexes used in a color developing solution is in the concentration range of about 0.1 to about 50 g, preferably about 1 g to about 15 g per 1 l of the color developing solution.

Light-sensitive silver halide color photographic materials comprising compound of formula (I) according to this invention may also be effectively processed by a color developing solution containing an aromatic primary amino color developing agent and, if desired, said color developing agent being such as to be received in a sensitive layer during color development and to be transferred to an amplifying bath and then contacting the developed materials with the amplifying bath containing such oxidant, as described above, for example, a cobalt complex having 6 coordination numbers. As a preferred other oxidant for this object, a hydrogen peroxide aqueous solution which is disclosed in JLOP No. 16,023/1976 can also be effectively used. Silver halide development inhibitors are preferred to be contained besides oxidants in such an amplifying solution. By doing so, one is enabled to carry out amplification even under room light. According to this operation, dye forming can be checked and stopped at a desired dye density. Preferred development inhibitors are water soluble bromides such as potassium bromide and heterocyclic compounds such as tetrazole, azaindene and triazole containing no mercapto group or no ionic iodide.

A concentration of a cobalt complex in an amplifying solution is generally in the range of about 0.2 g to about 20 g/l, most preferably about 1 g to about 15 g/l and that of the hydrogen peroxide solution about 0.01 to 10%, most preferably 0.5 to 5%. In the case of water soluble bromide as a development inhibitor, it is generally contained in an amount of about 1 g to about 40 g/l in the amplifying solution and a development inhibitor comprising a heterocyclic compound can generally be used in a concentration of 0.01 g to about 3 g/l. The amplifying bath generally can be used in a pH range of 6 to 14, preferably 8 to 12.

To the amplifying solution, there can be contained, besides said development inhibitors, if necessary, development accelerators, stabilizers, water softeners, solubilizing agents, surfactants, thickeners, agents for preventing the unevenness, etc.

This invention will be illustrated in detail by following examples but is not meant to limit the scope of this invention.

EXAMPLE 1

The respective magenta couplers and the respective exemplified compounds of this invention (or known compounds) as shown in Table 1-1 were dissolved in the solvent shown in the same Table and 120 mg of 2,5-di-t-octylhydroquinone was dissolved therein. The thus obtained solution was added to a 5% aqueous gelatin solution containing 2.5 g of sodium dodecylbenzenesulfonate and then dispersed therein by a homogenizer. The dispersed liquid thus obtained was added to 1,000 ml of a green sensitive silver chlorobromide emulsion (silver halide: 40 mol. %), and 10 ml of a 2% methanolic solution of N,N',N"-triacryloyl-6H-s-triazine was added thereto. Thereafter, the resulting mixture was coated on polyethylene coated paper and dried to obtain a sample of a light-sensitive silver halide color photographic material, which was then wedge-exposed. After processed according to the method described before, the photographic material was exposed to sun light for 2 months. Percentage of densities after exposure (referred to as D) against densities before exposure (referred to as Do); that is, D/Do×100 was measured by Sakura color densitometer (manufactured by Konishiroku Photo Ind. Co., Ltd.), as to the rate of resulting dye with green light and the Y-stain increasing rate in unexposed part with blue light. The results were shown in Table 1-2.

TABLE 1-1

| Sample No. | couplers and their added amounts (g) | anti-fading agents and their added amounts (g) | high-boiling solvents and their amnts. used (ml) | low-boiling solvents & their amnts. used (ml) |
|---|---|---|---|---|
| 1 | (M-1) 36 | — | DBP 36 | EA 100 |
| 2 | " " | known compound (I) 8 | " " | " " |

TABLE 1-1-continued

| Sample No. | couplers and their added amounts (g) | anti-fading agents and their added amounts (g) | high-boiling solvents and their amnts. used (ml) | low-boiling solvents & their amnts. used (ml) |
|---|---|---|---|---|
| 3 | " " | known compound (IV) 13 | " " | " " |
| 4 | " " | exemplified compound (7) 9.9 | " " | " " |
| 5 | " " | exemplified compound (11) 8.5 | " " | " " |
| 6 | (M-3) 39 | — | TPP 39 | " " |
| 7 | " " | known compd (III) 6 | " " | " " |
| 8 | " " | exemp. compd (43) 8.4 | " " | " " |
| 9 | " " | exemp. compd (14) 11 | " " | " " |
| 10 | (M-4) 39 | — | DBP 19 TCP 19 | MA " |
| 11 | " " | known compd (II) 4.4 | DBP 19 TCP 19 | " " |
| 12 | " " | exemp. compd (17) 6 | DBP 19 TCP 19 | " " |
| 13 | " " | exemp. compd (7) 4.8 (8) 4.8 | DBP 19 TCP 19 | " " |
| 14 | " " | exemp. compd (39) 9.9 | DBP 19 TCP 19 | " " |

DBP: dibutyl phthalate, TCP: tricresyl phosphate,
TPP: triphenyl phosphate, EA: ethyl acetate,
MA: methyl acetate
known compound (I):

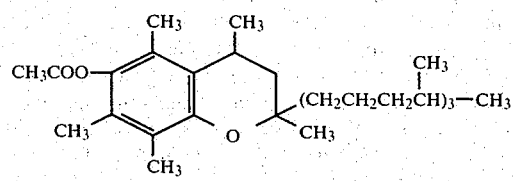

(a compound described in JLOP No. 27333/1976)
known compound (II):

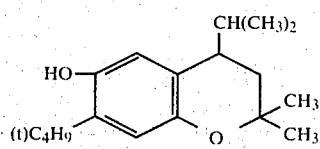

(a compound described in U.S. Pat. No. 3,432,300)
known compound (III):

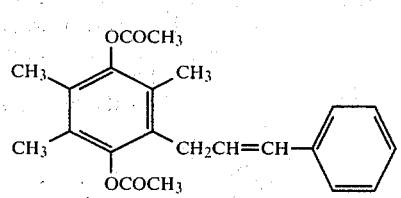

(a compound described in JLOP No. 14751/1977)
known compound (IV):

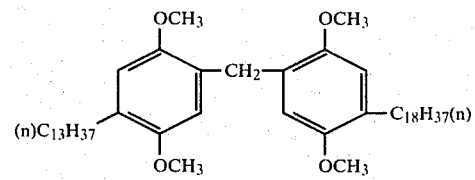

(a compound described in U.S. Pat. No. 2,735,765)

TABLE 1-2

| Sample No. | rate of residual dye | Y-stain increasing rate |
|---|---|---|
| 1 | 30 | 2,200 |
| 2 | 42 | 1,800 |
| 3 | 45 | 1,700 |
| 4 | 65 | 1,300 |
| 5 | 70 | 1,240 |
| 6 | 29 | 2,300 |
| 7 | 35 | 2,000 |
| 8 | 76 | 1,430 |
| 9 | 85 | 1,360 |
| 10 | 42 | 2,900 |
| 11 | 60 | 2,300 |
| 12 | 69 | 1,560 |
| 13 | 76 | 1,630 |
| 14 | 73 | 1,580 |

From Table 1-2, the following will be understood: the compound of this invention is excellent in the anti-fading effect for a magenta dye image, which effect is superior to that of anti-fading agents which have hitherto been known; and the compound of this invention effectively prevents a Y-stain in unexposed part and shows an excellent effect over a long period of time.

EXAMPLE 2

The respective yellow couplers and the respective exemplified compounds of this invention as shown in Table 2-1 were dissolved in the solvent shown in the same Table, and 150 mg of 2,5-di-t-octylhydroquinone was dissolved therein. The obtained solution was added to 500 ml of a 5% aqueous gelatin solution and then dispersed by a homogenizer. The dispersed liquid thus obtained was added to 1,000 ml of a blue sensitive silver chlorobromide emulsion (silver chloride: 10 mol. %) and 10 ml of a 5% methanolic solution of triethylenephosphonamide was added thereto as a hardener. The mixture thus obtained was coated on a polyethylene coated paper to obtain a sample of a light-sensitive silver halide photographic material. After processed in the same manner as in Example 1, the photographic material was exposed to a xenon fadometer for 100 hours. Measurements were conducted in the same manner as in Example 1 except that the dye density was measured. The results of Table 2-2 were obtained.

As seen clearly from Table 2-2, publicly-known compounds do not show any effect for preventing the fading of yellow dye images but show rather an effect for accelerating the fading. On the contrary to that, the compounds of this invention not only show an excellent effect for preventing also the fading of yellow dye images but also can prevent effectively the Y-stain in unexposed part.

TABLE 2-1

| Sample No. | couplers and their added amounts (g) | | anti-fading agents and their added amounts (g) | | high-boiling solvents and their amnts. | | low-boiling solvents & their amnts. | |
|---|---|---|---|---|---|---|---|---|
| | | | | | used | (ml) | used | (ml) |
| 1 | (Y-3) | 61 | — | — | DBP | 61 | EA | 120 |
| 2 | " | " | known compd. (I) | 16 | " | " | " | " |
| 3 | " | " | exemp. compd. (16) | 24.3 | " | " | " | " |
| 4 | " | " | exemp. compd. (25) | 29.3 | " | " | " | " |
| 5 | (Y-5) | 76 | — | — | " | " | " | " |
| 6 | " | " | known compd. (III) | 13.4 | " | " | " | " |
| 7 | " | " | exemp. compd. (11) | 20 | " | " | " | " |
| 8 | " | " | exemp. compd. (26) | 35 | TCP | " | " | " |

TABLE 2-2

| Sample No. | rate of residual dye | Y-stain increasing rate |
|---|---|---|
| 1 | 57 | 139 |
| 2 | 56 | 130 |
| 3 | 70 | 110 |
| 4 | 71 | 119 |
| 5 | 89 | 128 |
| 6 | 60 | 129 |
| 7 | 93 | 112 |
| 8 | 95 | 117 |

EXAMPLE 3

In a mixture of 40 g of dibutyl phthalate (DBP) and 120 g of ethyl acetate (EA) were dissolved 46 g of a cyan coupler (C-1), 200 mg of 2,5-di-t-octylhydroquinone and an anti-fading agent (shown in Table 3 with respect to kind and amount to be used). The obtained solution was added to 500 ml of a 5% aqueous gelatin solution containing sodium dodecylbenzenesulfonate and then dispersed by a homogenizer. The dispersed liquid thus obtained was added to 1,000 ml of a red sensitive silver chlorobromide emulsion containing 20 mol. % of silver chloride and then 20 ml of a 4% aqueous solution of sodium 2,4-dichloro-6-hydroxy-s-triazine was added thereto as a hardener. The obtained mixture was coated on a polyethylene coated paper to obtain a sample of a light-sensitive silver halide photographic material. Subsequently, a sample was prepared in the same manner as mentioned above except that 45 g of a cyan coupler (C-3) was used in place of 46 g of a cyan coupler (C-1). After processed in the same manner as in Example 1, these samples were exposed to sun light for 2 weeks. Measurements of the dye densities were conducted in the same manner as in Example 1 except that a red light was used. The results were shown in Table 3.

As is clear from Table 3, it will be understood that the compounds of this invention show better effect for preventing the discoloration of cyan images as compared with known anti-fading agents for dye images.

TABLE 3

| anti-fading agents & their amounts added (g) | | rate of residual dye cyan coupler | |
|---|---|---|---|
| | | C-1 | C-3 |
| 1 | — | 80 | 87 |
| 2 | exemplified compd. (7) 16 | 90 | 93 |
| 3 | exemplified compd. (25) 23.7 | 92 | 92 |
| 4 | known compd. (I) 12.9 | 81 | 88 |
| 5 | known compd. (II) 7.3 | 82 | 88 |
| 6 | known compd. (III) 9 | 83 | 86 |

EXAMPLE 4

Each of the following layers was coated in turn on a polyethylene coated paper to prepare a sample of a light-sensitive silver halide photographic material.

(Sample 1)

First layer:

A blue sensitive silver halide emulsion layer comprising a silver chlorobromide emulsion containing 10 mol. % of silver chloride, which emulsion contains 400 g of gelatin per mole of silver halide; was sensitized by using $2.5 \times 10^{-4}$ mole of a sensitizing dye of the following formula:

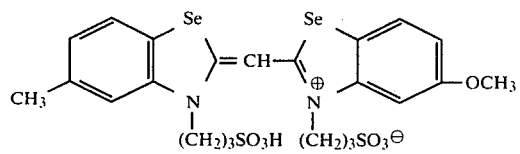

per mole of silver halide; contains $2 \times 10^{-1}$ mole of a yellow coupler (Y-6) dissolved and dispersed in DBP per mole of silver halide; and was coated on a support so that the amount of silver may be 400 mg/m².

Second layer:

A gelatin layer which was coated so that the thickness of the dry layer may be 1μ.

Third layer:

A green sensitive silver halide emulsion layer comprising a silver chlorobromide emulsion containing 40 mol. % of silver chloride, which emulsion contains 500 g of gelatin per mole of silver halide; has been sensitized by using $2.5 \times 10^{-4}$ mole of a sensitizing dye of the following formula:

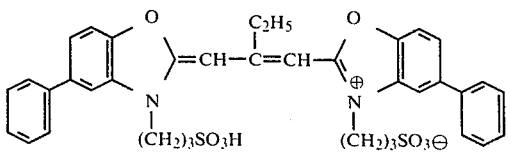

per mole of silver halide; contains $2 \times 10^{-1}$ mole of a magenta coupler (M-14) dissolved and dispersed in TCP per mole of silver halide; and has been coated so that the amount of silver may be 350 mg./m².

Fourth layer:

A gelatin layer having a thickness of 1μ. and containing 30 mg./m² of 2,5-di-t-octylhydroquinone dissolved and dispersed in DBP and 700 mg/m² of 2-(2'-hydroxy-3', 5'-di-t-butylphenyl)benzotriazole Fifth layer:

A red sensitive silver halide emulsion layer comprising a silver chlorobromide emulsion containing 20 mol. % of silver halide, which emulsion contains 500 g of gelatin per mole of silver halide; has been sensitized by using $2.5 \times 10^{-4}$ mole of a sensitizing dye of the following formula:

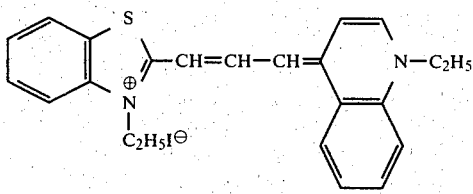

per mole of silver halide; contains $2 \times 10^{-1}$ mole of a cyan coupler (C-3) dissolved and dispersed in TCP per mole of silver halide; and has been coated so that the amount of silver may be 500 mg/m².

Sixth layer:

A gelatin layer of 1μ in dry thickness has been coated (protective layer).

Each of the silver halide emulsions used in the first, third and fifth layers was prepared according to the method described in Japanese Patent Publication No. 7772/1971; subjected to chemical sensitization by using sodium thiosulfate pentahydrate; and incorporated with 4-hydroxy-6-methyl-1,3,3a,7-tetrazaindene as a stabilizer, bis (vinylsulfonylmethyl)ether as a hardener and saponin as a coating aid.

To each of the first, third and fifth light-sensitive layer was added the compound (exemplified compound No. 16) of the present invention in an amount of 30 mol. % against the coupler contained in each layer and dispersed to prepare Sample 2.

In place of the exemplified compound of this invention which was used in the preparation of Sample 2 above, the same amount of each known compounds (I), (II) and (III) was used to prepare Samples 3, 4 and 5, respectively.

To the third light-sensitive layer of Sample 1 was added a coupler and compounds No. 10 to 26 in an amount of 30 mol. % against the coupler and dispersed to prepare Samples 6 and 7, respectively.

In place of the exemplified compound of this invention which was used in Sample 6, the same amount of known compound (I), (II) or (III) was used to prepare Samples 8, 9 and 10, respectively.

Each of the Samples as prepared above was wedge-exposed to a blue, green or red light and processed according to the procedure in Example 1. After exposure for 300 hours, the dye densities and the Y-stain increasing rates were measured with xenon fadometer. The results obtained were shown in Table 4.

TABLE 4

| Sample No. | rate of residual dye | | | Y-stain increasing rate |
|---|---|---|---|---|
| | yellow | magenta | cyan | |
| 1 | 65 | 45 | 70 | 410 |
| 2 | 85 | 90 | 89 | 200 |
| 3 | 65 | 55 | 68 | 320 |
| 4 | 50 | 70 | 70 | 290 |
| 5 | 64 | 50 | 67 | 380 |

TABLE 4-continued

| Sample No. | rate of residual dye | | | Y-stain increasing rate |
|---|---|---|---|---|
| | yellow | magenta | cyan | |
| 6 | 66 | 90 | 71 | 220 |
| 7 | 65 | 92 | 71 | 210 |
| 8 | 64 | 53 | 71 | 330 |
| 9 | 66 | 66 | 69 | 300 |
| 10 | 65 | 48 | 70 | 390 |

As is clear from Table 4, it will be understood that known anti-fading agents for dye images do not show any anti-fading effect on dye images except for magenta dye image at all, or tend to accelerate the fading and that, on the contrary, the compounds of this invention show an excellent effect not only for magenta dye images but also for yellow and cyan dye images, and thus the compounds of this invention are extremely excellent anti-fading agents for dye images.

EXAMPLE 5

In a mixture of 11 g of DBP and 30 g of EA was dissolved 12 g (30 mol. % against the coupler) of Compd. No. 24. The resulting solution was added to 120 ml of a 5% aqueous gelatin solution containing sodium dodecylbenzenesulfonate and then dispersed by a homogenizer. The dispersed liquid thus obtained was added to 300 ml of a green sensitive silver chlorobromide emulsion (silver chloride: 30 mol. %), coated on a polyethylene coated paper and dried to obtain a sample of a light-sensitive silver halide photographic material.

The color photographic material was wedge-exposed by means of a sensitometry method and processed in the following order at 24° C.:

| Processing | min. |
|---|---|
| First development | 5 |
| Water washing | 4 |
| Exposure | |
| Color development | 3 |
| Water washing | 4 |
| Bleaching | 4 |
| Fixing | 4 |
| Water washing | 10 |

In the above first development, color development, bleaching and fixing, the following compositions were employed:

| First development composition: | | |
|---|---|---|
| Anhydrous sodium bisulfite | 8.0 | g |
| Phenidone | 0.35 | g |
| Anhydrous sodium sulfite | 37.0 | g |
| Hydroquinone | 5.5 | g |
| Anhydrous sodium carbonate | 28.2 | g |
| Sodium thiocyanate | 1.38 | g |
| Anhydrous sodium bromide | 1.30 | g |
| Potassium iodide (0.1% aqueous solution) | 13.0 | ml |
| Water to make | 1 | l (pH 9.9) |
| Color developer composition: | | |
| Anhydrous sodium sulfite | 10.0 | g |
| N,N-diethyl-p-phenylenediamine hydrochloride | 3.0 | g |
| Magenta coupler (M-19) | 1.5 | g |
| Water to make | 1 | l |
| pH 11.5 with sodium hydroxide | | |
| Bleaching solution composition: | | |
| Anhydrous sodium bromide | 43.0 | g |
| Potassium ferricyanide | 165.0 | g |
| Borax ($Na_2B_4O_7 \cdot 10H_2O$) | 1.2 | g |

| | -continued | | |
|---|---|---|---|
| Water to make | | 1 | l |
| Fixing solution composition: | | | |
| Sodium thiosulfate pentahydrate | | 200 | g |
| Anhydrous sodium sulfite | | 10.0 | g |
| Anhydrous bisodium phosphate | | 15.0 | g |
| Water to make | | 1 | l |

The color photographic material so processed was tested in the same way as in Example 1 except for exposure for 100 hours with a xenon fadometer to measure a rate of residual dye and a Y-stain increasing rate. For comparison, known compound (III) was used in the same amount in place of the compound of this invention and no compound of this invention was used in the blank.

The results obtained were listed in Table 5.

TABLE 5

| Sample No. | anti-fading agent | rate of residual dye | Y-stain increasing rate |
|---|---|---|---|
| 1 | Blank | 64 | 485 |
| 2 | exemplified compound (24) | 95 | 110 |
| 3 | known compound (III) | 86 | 160 |

From Table 5 above, it will be understood that the compound of this invention prevents a Y-stain even in the case where a coupler is not incorporated in a light-sensitive silver halide photographic material (i.e., coupler-in-developer type light-sensitive silver halide photographic material) and shows an excellent anti-fading effect.

EXAMPLE 6

To a mixture of 20 ml of DBP and 40 ml of EA was added 20 g of the respective anti-fading agent for dye images shown in Table 6. The solution was added to a mixture of 2,000 ml of a 10% aqueous gelatin and 200 ml of a 5% aqueous sodium dodecylbenzenesulfonate, and then dispersed with a homogenizer. After the dispersed liquid thus obtained was coated on a polyethylene coated paper and dried, the existence of the precipitation of crystals on the sample thus obtained was checked with an optical microscope.

The results were shown in Table 6.

TABLE 6

| Sample No. | anti-fading agent for dye image | | precipitation of crystals |
|---|---|---|---|
| 1 | known compd | (V) | Yes |
| 2 | exemplified compound | (1) | No |
| 3 | exemplified compound | (7) | No. |
| 4 | exemplified compound | (10) | No |
| 5 | exemplified compound | (29) | No | known compound (V):

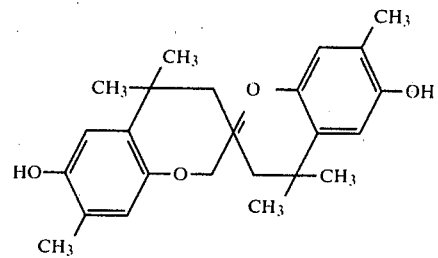

(a compound described in Japanese Patent Publication No. 20977/1974)

As seen clearly from Table 6, the compounds of this invention show a dispersion stability since the samples (No. 2-5) according to this invention did not give any precipitation of crystals even after they had been allowed to stand for 2 months.

EXAMPLE 7

In a mixture of 25 ml of DBP and 70 ml of EA was dissolved 36 g of a magenta coupler (M-20) and 11 g of the respective compound of this invention listed in Table 7. The resulting solution was added to 500 ml of a 5% aqueous gelatin solution containing 2.5 g of sodium dodecylbenzenesulfonate, and then dispersed by a homogenizer. The dispersed liquid thus obtained was added to a green sensitive silver chlorobromide (silver bromide: 80 mol. %) and 10 ml of a 2% methanolic solution of N,N', N"-triacryloyl-6H-s-triazine as a hardener was added thereto. The resulting emulsion was coated on a polyethylene coated paper and dried. The sample thus obtained was subjected to photographic processing, after exposure, in the same way as in Example 1. Thereafter, the sample was subjected to sensitometry in the usual manner by using Sakura-color-densitometer PD-6 (manufactured by Konishiroku Photo Industries Co., Ltd.) to measure sensitivity, $\gamma$, fog and maximum density.

The results were shown in Table 7. Sensitivities are indicated as relative sensitivities, assuming that the sensitivity of Sample No. 1 was 100.

TABLE 7

| Sample No. | exemplified compounds | sensitivity | $\gamma$ | fog | maximum color density |
|---|---|---|---|---|---|
| 1 | — | 100 | 3.50 | 0.04 | 2.85 |
| 2 | (2) | 101 | 3.49 | 0.03 | 2.86 |
| 3 | (20) | 100 | 3.51 | 0.03 | 2.86 |
| 4 | (36) | 100 | 3.50 | 0.03 | 2.85 |
| 5 | (39) | 102 | 3.51 | 0.03 | 2.86 |
| 6 | (53) | 101 | 3.50 | 0.03 | 2.86 |

As is clear from Table 7, the compounds of this invention do not affect badly the photographic characteristics. It is very important that a novel compound does not affect the photographic characteristics when it is added in order to improve other properties than the photographic characteristics. In this sense, it will be understood that the compounds of this invention are excellent photographic additives.

EXAMPLE 8

The respective magenta couplers and the respective compounds of this invention or a known anti-fading agent as shown in Table 8-1 were dissolved in the solvent shown in the same Table and 120 mg of 2,5-di-t-octylhydroquinone was dissolved therein.

The thus obtained solution was added to a 5% aqueous gelatin solution containing 2.5 g of sodium dodecyl-benzene-sulfonate and then dispersed therein by a homogenizer. The thus obtained dispersion was added into 1,000 cc of a green sensitive silver chloride-bromide emulsion (containing 40 mol. % of silver chloride). 10 ml of 3% aqueous methanol solution of reaction product of tetrakis (vinyl sulfonyl methyl) methane and potassium 2-amino methane sulfonate (mol. ratio 1:1) was added thereto. Thereafter, the resulting mixture was coated on a paper covered by polyethylene and then dried to obtain a sample of a light-sensitive silver halide photographic material.

These samples were exposed to light through an optical wedge according to a sensitometry method, and then processed as follows:

| Processing (at 33° C.) | |
| --- | --- |
| | Processing time |
| 1. Color development | 3 min. 30 sec. |
| 2. Bleaching and fixing | 1 min. 30 sec. |
| 3. Washing | 3 min. 30 sec. |
| Composition of color developing solution: | |
| Benzyl alcohol | 15 ml |
| Sodium hexamethaphosphate | 2.5 g |
| Anhydrous sodium sulfite | 1.9 g |
| Sodium bromide | 1.4 g |
| Potassium bromide | 0.5 g |
| Borax (Na$_2$B$_4$O$_7$ . 10H$_2$O) | 39.1 g |
| N-ethyl-N-β-methane sulfonamide ethyl-3-methyl-4-amino-aniline sulfate | 4.5 g |
| Whitex BB (50% solution) (Trade name by Sumitomo Chem. Co.) | 2 ml |
| Water to make | 1 l |
| pH was adjusted to pH 10.2 by using sodium hydroxide | |
| Composition of bleaching and fixing solution: | |
| The composition was as set forth before. | |

The thus processed samples were exposed to sun light through transparent window glass for three months. Measurements were conducted in the same manner as Example 1. The results of Table 8-2 were obtained.

From Table 8-2, the following will be understood: the compounds of this invention are excellent in the anti-fading effect for a magenta dye image, which effect is superior to that of known anti-fading agents: and the compounds of this invention effectively prevent a Y-stain in unexposed part.

TABLE 8-1

| Sample No. | couplers and their added amounts (g) | | anti-fading agents and amounts (g) | high-boiling solvents and their amnts. used (ml) | | low-boiling solvents & their amnts. used (ml) | |
| --- | --- | --- | --- | --- | --- | --- | --- |
| 1 | M-20 | 39 | — | DBP | 39 | EA | 80 |
| 2 | " | " | known cmpd. (IV) 13.0 | " | " | " | " |
| 3 | " | " | exemp. cmpd. (51) 9.3 | " | " | " | " |
| 4 | " | " | exemp. cmpd. (55) 7.0 | " | " | " | " |
| 5 | " | " | exemp. cmpd. (65) 7.9 | " | " | " | " |

TABLE 8-2

| Sample No. | rate of residual dye | Y-stain increasing rate |
| --- | --- | --- |
| 1 | 45 | 2,000 |
| 2 | 57 | 1,850 |
| 3 | 70 | 1,200 |
| 4 | 77 | 1,250 |
| 5 | 75 | 1,000 |

We claim:

1. A color photographic material comprising a support and a hydrophilic layer containing a dye image which material contains a compound represented by the following formula (I):

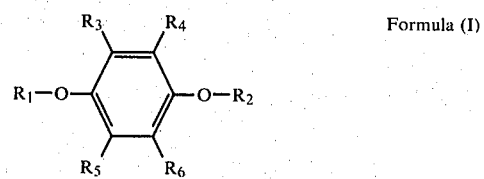

Formula (I)

wherein $R_1$ and $R_2$ each represent an alkyl group, an alkenyl group, a cycloalkyl group, an aryl group or a heterocyclic ring, and when $R_1$ and $R_2$ both are an alkyl group, the sum of the carbon atoms of said alkyl group is not less than 3; two of $R_3$, $R_4$, $R_5$ and $R_6$ represent an alkyl, alkenyl or alkoxy group of up to 32 carbon atoms and the other two represent hydrogen; and each of said compound does not substantially react with the oxidized form of a developer to form a coloring dye.

2. A color photographic material according to claim 1 wherein the hydrophilic layer containing the compound.

3. A color photographic material according to claim 1 wherein the photographic material further comprises a layer adjacent to the hydrophilic layer, the adjacent layer containing the compound.

4. A color photographic material according to claim 1 wherein $R_1$ and $R_2$ each represent an alkyl group having 1 to 32 carbon atoms or an alkenyl group having 2 to 32 carbon atoms.

5. A color photographic material according to claim 1 wherein two of $R_3$, $R_4$, $R_5$ and $R_6$ each represent an alkyl group having 1 to 8 carbon atoms, an alkenyl group having 2 to 8 carbon atoms or an alkoxy group having 1 to 8 carbon atoms.

* * * * *